United States Patent
Joy et al.

(10) Patent No.: US 10,456,363 B2
(45) Date of Patent: Oct. 29, 2019

(54) MODIFIED CYCLODEXTRIN COATED MAGNETITE NANOPARTICLES FOR TARGETED DELIVERY OF HYDROPHOBIC DRUGS

(71) Applicant: COUNCIL OF SCIENTIFIC & INDUSTRIAL RESEARCH, New Delhi (IN)

(72) Inventors: Pattayil Joy, Maharashtra (IN); Jayaprabha Kunnoth Naduvilidam, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/544,164

(22) PCT Filed: Jan. 15, 2016

(86) PCT No.: PCT/IN2016/050018
§ 371 (c)(1),
(2) Date: Jul. 17, 2017

(87) PCT Pub. No.: WO2016/113762
PCT Pub. Date: Jul. 21, 2016

(65) Prior Publication Data
US 2018/0008552 A1    Jan. 11, 2018

(30) Foreign Application Priority Data
Jan. 15, 2015    (IN) .............................. 124/DEL/2015

(51) Int. Cl.
| | | |
|---|---|---|
| *A61K 31/12* | (2006.01) | |
| *A61K 41/00* | (2006.01) | |
| *A61K 33/26* | (2006.01) | |
| *A61K 9/51* | (2006.01) | |
| *A61K 49/18* | (2006.01) | |
| *A61K 47/69* | (2017.01) | |
| *A61K 36/9066* | (2006.01) | |
| *A61K 31/337* | (2006.01) | |
| *A61K 31/475* | (2006.01) | |
| *A61K 31/519* | (2006.01) | |
| *A61K 31/704* | (2006.01) | |

(52) U.S. Cl.
CPC .......... *A61K 9/5192* (2013.01); *A61K 9/5161* (2013.01); *A61K 31/12* (2013.01); *A61K 31/337* (2013.01); *A61K 31/475* (2013.01); *A61K 31/519* (2013.01); *A61K 31/704* (2013.01); *A61K 33/26* (2013.01); *A61K 36/9066* (2013.01); *A61K 41/00* (2013.01); *A61K 47/6923* (2017.08); *A61K 47/6939* (2017.08); *A61K 47/6951* (2017.08); *A61K 49/1863* (2013.01)

(58) Field of Classification Search
None
See application file for complete search history.

(56) References Cited

U.S. PATENT DOCUMENTS

2013/0245357 A1* 9/2013 Chauhan ............ A61K 49/1845
600/12
2014/0369938 A1* 12/2014 Pattayil ............... A61K 9/0009
424/9.32

FOREIGN PATENT DOCUMENTS

| WO | WO 2012/078745 A1 | 6/2012 | | |
|---|---|---|---|---|
| WO | WO-2012078745 A1 * | 6/2012 | ......... | A61K 49/1845 |
| WO | WO 2013/108270 A1 | 7/2013 | | |
| WO | WO-2013108270 A1 * | 7/2013 | ........... | A61K 9/0009 |

OTHER PUBLICATIONS

Banerjee and Chen, "Magnetic Nanoparticles Grafted with Cyclodextrin for Hydrophobic Drug Delivery", Chem Mater 19: 6345-6349 (2007) (herein, Banerjee) (Year: 2007).*
Banerjee and Chen, "Magnetic nanoparticles grafted with cyclodextrin for hydrophobic drug delivery", Chem Mater 19: 6345-6349 (2007) (Year: 2007).*
Hegge et al., "Impact of Curcumin Supersaturation in Antibacterial Photodynamic Therapy—Effect of Cyclodextrin Type and Amount: Studies on Curcumin and Curcuminoides XLV", Amer Pharma Assoc J Pharm Sci 101: '524-1537 (2012) (Year: 2012).*
WIPO written opinion (Year: 2018).*
Huang et al.(Preparation of water-based-cyclodextrin /Fe3O4 magnetic fluid and its adsorption behavior for neutral red, Yingyong Huaxe, 2014, 31(5), 607-12) (Year: 2014).*
International Search Report issued in connection with PCT International Application No. PCT/IN2016/050018.
Written Opinion of the International Searching Authority issued in connection with PCT International Application No. PCT/IN2016/050018.
Banerjee, S. S., et al, "Magnetic Nanoparticles Grafted with Cyclodextrin for Hydrophobic Drug Delivery", Chemistry of Materials, Dec. 11, 2007, vol. 19, No. 25, pp. 6345-6349, American Chemical Society, USA.
Jayaprabha, K. N., et al, "Citrate modified β-cyclodextrin functionalized magnetite nanoparticles: A biocompatible platform for hydrophobic drug delivery", RSC Advances, Feb. 17, 2015, vol. 5, No. 28, pp. 22117-22125, Royal Society of Chemistry, GBR.

* cited by examiner

*Primary Examiner* — Alton N Pryor
(74) *Attorney, Agent, or Firm* — John P. White; Cooper & Dunham LLP

(57) ABSTRACT

The invention discloses a composition comprising surface modified iron oxide nanoparticles with citric acid modified cyclodextrin with a hydrodynamic diameter of less than 10 nm and a hydrophobic molecule.
The composition finds use in targeted delivery of a hydrophobic drug and as contrast agent in imaging applications.

5 Claims, 8 Drawing Sheets

Figure 5
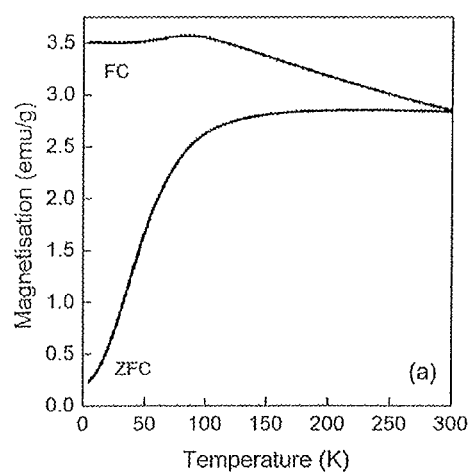
FIGURE 5A
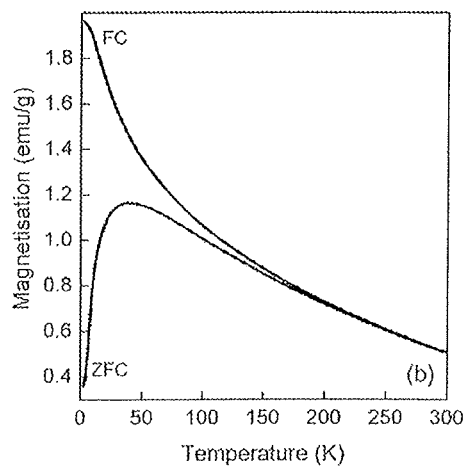
FIGURE 5B

MODIFIED CYCLODEXTRIN COATED MAGNETITE NANOPARTICLES FOR TARGETED DELIVERY OF HYDROPHOBIC DRUGS

CROSS-REFERENCE TO RELATED APPLICATIONS

This application is a § 371 national stage of PCT International Application No. PCT/IN2016/050018, filed Jan. 15, 2016, claiming priority of Indian Patent Application No. IN 124/DEL/2015, filed Jan. 15, 2015, the contents of each of which are hereby incorporated by reference into the application.

FIELD OF THE INVENTION

The present invention relates to Beta-cyclodextrin-citrate coated magnetic nanoparticles encapsulating a hydrophobic molecule. Particularly the present relates to the process for preparation of Beta-cyclodextrin-citrate coated magnetic nanoparticles. More particularly the present invention relates to hydrophobic drug loaded Beta-cyclodextrin-citrate coated magnetic nanoparticles and process of preparation thereof.

Additionally the present invention relates to the use of hydrophobic drug loaded Beta-cyclodextrin-citrate coated magnetic nanoparticles as a multifunctional probe that can be used in targeted drug delivery, magnetic hyperthermia and contrast enhancement agent in MRI.

BACKGROUND OF THE INVENTION

Drug targeting and release is an area of intense research. Continuous efforts are being made to develop controlled drug release system because appropriate dosage decides the therapeutic efficiency of the drugs. The main target of the current drug delivery research are specific targeting and delivery of drugs, reduction in toxicity while maintaining the therapeutic effects, greater safety and biocompatibility. Drug delivery systems developed by nanotechnology researchers include polymeric micelles, polymeric nanoparticles, magnetic nanoparticles, liposomes and dendrimers. Of all these iron oxide based magnetic nanoparticles are of interest in drug delivery due to the benefit of targeting the carrier by an external magnetic field. Iron oxide nanoparticles coated with suitable surfactants also act as a multi-functional platform which can be simultaneously used as contrast agents in magnetic resonance imaging (MRI), magnetic hyperthermia and drug delivery. Even though there are various reports on the biomedical application of magnetite nanoparticles, delivery of hydrophobic drug without losing its therapeutic efficacy is of importance. The delivery of these drugs to the target site is suggested through different carriers like polymeric micelles, silica nanoparticles and cyclodextrin derivatives. Of these cyclodextrins which have a hydrophobic cavity can be an efficient candidate for entrapment of hydrophobic drug.

Article titled, "Novel method for preparation of β-cyclodextrin/grafted chitosan and it's application" by K. El-Tahlawy et. al in Carbohydrate Polymers, 2006, 63, 385-392 reports a novel technique for preparation of β-cyclodextrin-grafted chitosan by reacting β-cyclodextrin citrate (β-CD citrate) with chitosan. β-Cyclodextrin citrate was synthesized by esterifying β-cyclodextrin (β-CD) with citric acid (CA) in presence or absence of sodium hypophosphite as a catalyst in a semidry process. Chitosan and β-cyclodextrin/grafted chitosan, having different molecular weights, were evaluated as antimicrobial agents for different microorganisms such as, *Bacillus megaterium, Pseudomonas fragi, Bacillus cereus Staphylococcus aureus, Escherichia E coli* and *Aeromonas hydra*.

Article titled, "Magnetic Nanoparticles Grafted with Cyclodextrin for Hydrophobic Drug Delivery" by Shashwat S. Banerjee and Dong-Hwang Chen in Chem. Mater. 2007, 19, 6345-6349 reports a novel magnetic nanocarrier, cyclodextrin (CD)-citrate-gum arabic modified magnetic nanoparticles (GAMNPs), for hydrophobic drug delivery fabricated by grafting the citrate-modified CD onto the GAMNPs via carbodiimide activation. The product had a mean diameter of 14.6 nm and a mean hydrodynamic diameter of 26.2 nm. The amount of CD grafted on the GAMNPs was determined to be 28.7 mg/g by the thermogravimetric analysis. The feasibility of using CD-citrate-GAMNPs as a carrier for hydrophobic drug delivery was demonstrated by investigating the formation of the inclusion complex and the in vitro release profile using ketoprofen as a model hydrophobic drug. Also, the presence of surfactant (sodium dodecyl sulfate, SDS) led to a decrease in the inclusion of ketoprofen because the linear structure of SDS made it easier to enter the cavity of CD as compared with the less linear ketoprofen.

Article titled, "Multi-functional magnetic nanoparticles for magnetic resonance imaging and cancer therapy" by Murali M. Yallapu, Shadi F. Othman, Evan T. Curtis b, Brij K. Gupta, Meena Jaggi, Subhash C. Chauhan in Biomaterials 32 (2011) 1890-1905 reports a multi-layer approach for the synthesis of water-dispersible superparamagnetic iron oxide nanoparticles for hyperthermia, magnetic resonance imaging (MRI) and drug delivery applications. In this approach, iron oxide core nanoparticles were obtained by precipitation of iron salts in the presence of ammonia and provided b-cyclodextrin and pluronic polymer (F127) coatings. This formulation (F127250) was highly water dispersible which allowed encapsulation of the anti-cancer drug(s) in b-cyclodextrin and pluronic polymer for sustained drug release. The F127250 formulation has exhibited superior hyperthermia effects over time under alternating magnetic field compared to pure magnetic nanoparticles (MNP) and b-cyclodextrin coated nanoparticles (CD200). Additionally, the improved MRI characteristics were also observed for the F127250 formulation in agar gel and in cisplatin resistant ovarian cancer cells (A12780CP) compared to MNP and CD200 formulations. Furthermore, the drug loaded formulation of F127250 exhibited many folds of imaging contrast properties. Due to the internalization capacity of the F127250 formulation, its curcumin-loaded formulation (F127250-CUR) exhibited almost equivalent inhibition effects on A2780CP (ovarian), MDA-MB-231 (breast), and PC-3 (prostate) cancer cells even though curcumin release was only 40%. F127250-CUR also exhibited haemo compatibility, suggesting a nanochemotherapuetic agent for cancer therapy.

Article titled, "Water-dispersible ascorbic-acid-coated magnetite nanoparticles for contrast enhancement in MRI" by V. Sreeja, K. N. Jayaprabha and P. A. Joy in Applied Nanoscience April 2015, Volume 5, Issue 4, pp 435-441 (First online on April 2014) reports Superparamagnetic iron oxide nanoparticles of size ~5 nm surface functionalized with ascorbic acid (vitamin C) form a stable dispersion in water with a hydrodynamic size of ~30 nm. NMR relaxivity studies show that the ascorbic-acid-coated superparamagnetic iron oxide aqueous nanofluid is suitable as a contrast enhancement agent for MRI applications, coupled with the excellent biocompatibility and medicinal values of ascorbic acid.

Article titled, "Curcumin Encapsulated Superparamagnetic Iron Oxide Based Nanofluids for Possible Multifunctional Applications" by K. N. Jayaprabha and P. A. Joy in J. Nanofluids, 2014, 3, 1-7 reports synthesis of Curcumin coated ultra-small superparamagnetic iron oxide nanoparticles (USPIONs) of size 3 nm. Relaxivity measurements using nuclear magnetic resonance (NMR) technique showed values similar to that reported for other established superparamagnetic iron oxide based contrast enhancement agents in magnetic resonance imaging (MRI). Thus, curcumin coated USPIONs are suitable as contrast enhancement agent in MRI along with the medicinal and fluorescent property of the curcumin shell, indicating the possible multifunctional applications.

Article titled, "Cyclodextrin-curcumin self-assembly enhances curcumin delivery in prostate cancer cells" by Murali Mohan Yallapua, Meena Jaggi, Subhash C. Chauhan in Colloids and Surfaces B: Biointerfaces 79 (2010) 113-125 reports a cyclodextrin (CD) mediated curcumin drug delivery system via encapsulation technique. Curcumin encapsulation into the CD cavity was achieved by inclusion complex mechanism. Curcumin encapsulation efficiency was improved by increasing the ratio of curcumin to CD. An optimized CD-curcumin complex (CD30) was evaluated for intracellular uptake and anti-cancer activity. Cell proliferation and clonogenic assays demonstrated that cyclodextrin-curcumin self-assembly enhanced curcumin delivery and improved its therapeutic efficacy in prostate cancer cells compared to free curcumin.

US20140369938A1 relates to curcumin coated magnetite nanoparticles, which are biocompatible, stable curcumin or its derivatives coated ultra-small superparamagnetic iron oxide nanoparticles (USPION) for biomedical applications. The invention further relates to a simple one-pot process for the synthesis of biocompatible, stable curcumin or its derivatives coated ultra-small superparamagnetic iron oxide nanoparticles in absence of a linker or binder. The average crystallite sizes of uncoated and coated samples are in the range of 7 nm and 4 nm respectively.

Article titled "A novel curcumin-artemisinin coamorphous solid: physical properties and pharmacokinetic profile" by Kuthuru Suresh, M. K. Chaitanya Mannava and Ashwini Nangia in RSC Adv., 2014, 4, 58357-58361 reports a curcumin-artemisinin coamorphous solid (1:1) prepared by rota-vaporization and a dramatic increase in the pharmacokinetic profile of curcumin.

But there is a still a need in the art to provide a suitable carrier for hydrophobic drugs that provides a targeted delivery of the drug to the site of action, such that the carrier possesses a cavity that is suitable to hold or lodge a small hydrophobic molecule such as a drug. It would be advantageous if such a carrier further can possess improved loading efficiency with regard to the small hydrophobic molecule.

OBJECTIVE OF THE INVENTION

Main objective of the present invention is to provide a suitable carrier for hydrophobic drugs, for targeted drug delivery, with a desired small hydro dynamic diameter.

Another objective of the invention is to provide a process of synthesis of a suitable carrier for hydrophobic drugs for targeted drug delivery.

SUMMARY OF THE INVENTION

In another embodiment of the present invention, said
Accordingly the present invention provides a Beta-cyclodextrin-citrate coated magnetic nanoparticles of size 3 to 10 nm.

In an embodiment, present invention provides a process for the preparation of Beta-cyclodextrin-citrate coated magnetic nanoparticles comprising the steps of:

i. dissolving β-cyclodextrin and citric acid in a ratio ranging between 3:1 to 5:2 in water followed by stirring the mixture at a temperature in a range of 70-80° C. for period in the range of 3-4 hrs to obtain a transparent solution;
ii. treating the transparent solution as obtained in step (i) with alcohol, followed by washing and drying at a temperature in the range of 60-70° C. for a period in the range of 24-26 hrs to obtain cyclodextrin-citrate complex;
iii. dissolving cyclodextrin-citrate complex as obtained in step (ii) in water to obtain a cyclodextrin-citrate solution;
iv. mixing ferric chloride hexahydrate and ferrous chloride tetrahydrate molar ratio ranging from 2:1 to 5:3 in water and ammonium hydroxide solution followed by stirring and washing to obtain magnetic nanoparticle;
v. redispersing the magnetic nanoparticles as obtained in step (iv) followed by adding the Cyclodextrin-citrate solution as obtained in step (iii) with stirring for period in the range of 4-5 hours at temperature in the range of 80-90° C. to obtain a stable dispersion;
vi. dialyzing the dispersion obtained in step (v) against water for a period in range of 3-4 days and at a temperature in the range of 60-70° C. to obtain coated solid nanoparticles;
vii. dispersing the coated nanoparticles obtained in step (vi) in water at the physiological pH to obtain Beta-cyclodextrin-citrate coated magnetite nanoparticles;

In still another embodiment of the present invention the said coated nanoparticles are useful for targeted drug delivery.

In yet another embodiment of the present invention the said coated nanoparticles are loaded with hydrophobic drugs.

In an embodiment, present invention provides a process for preparation of hydrophobic drugs loaded beta-cyclodextrin-citrate coated magnetic nanoparticles comprising the steps of:

a. dissolving curcumin in solvent followed by adding beta-cyclodextrin-citrate coated magnetite nanoparticles as obtained in claim 6 and stirring gently for 6-8 hrs to obtain a mixture;
b. stirring the mixture as obtained in step (a) for a period in the range of 8-12 hrs followed by centrifuging at 4000-5000 rpm for a period in the range of 5-8 minutes to followed by drying to obtain Curcumin loaded beta-cyclodextrin-citrate coated magnetite nanoparticles.

In yet another embodiment of the present invention the solvent used in step (a) is selected from acetone cyclohexane, DMSO, etc.

In yet another embodiment of the present invention the hydrophobic drugs are selected from curcumin, doxorubicin, taxol, methotrexate, vincritine and such like.

In yet another embodiment of the present invention wherein the drug loaded is curcumin.

In yet another embodiment of the present invention the coated nanoparticle is used as contrast agents in MRI Scanning.

Abbreviations
CIT—Citric acid
CD—β-cyclodextrin
CUR—Curcumin
CD-CIT—Cyclodextrin-citrate complex
Unmf—Uncoated magnetite nanoparticles
CITmf—Citric acid coated magnetite nanoparticles/nanofluids
CURmf—Curcumin coated magnetite nanoparticles/nanofluids
CDmf—CD-CIT coated magnetite nanoparticles/nanofluids
CDmf10, CDmf20, CDmf30—Curcumin loaded CDmf nanofluids by using 20 mg of CDmf and 10, 20 and 30 mg of curcumin, respectively
CD20—Curcumin loaded CD using 20 mg of curcumin
CD-CIT20—Curcumin loaded CD-CIT using 20 mg of curcumin

DETAILED DESCRIPTION OF THE INVENTION

Figure 1:
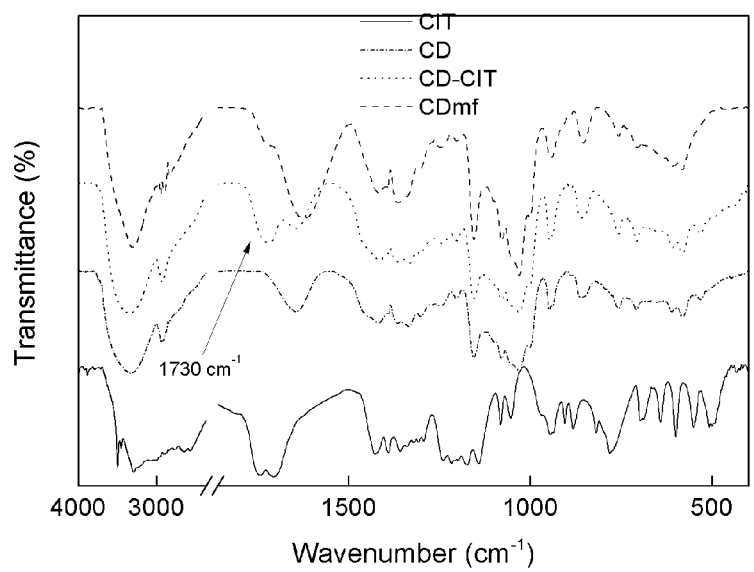
FIG. 1 depict IR spectra of citric acid (CIT), citric acid-cyclodextrin complex (CD-CIT), β-cyclodextrin (CD), citric acid (CIT) and the CD-CIT coated magnetite nanoparticles (CDmf).

The present invention provides a composition that can be used for more efficient loading/encapsulation of a hydrophobic molecule.

The composition comprises surface modified iron oxide nano particles, wherein the modification is done using an ester of an acid and a biocompatible entity. The acid used is citric acid and the biocompatible entity is β-cyclodextrin (CD).

The composition comprising the surface modification of iron oxide nanoparticles with the ester of citric acid and β-cyclodextrin and the mean size of 5 nm and the hydrodynamic size as obtained is 7.7 nm. The composition increases the encapsulation efficiency of curcumin into the cyclodextrin cavity and the drug can be targeted to the infected site by an external magnetic field. The CD-citrate coated nanoparticles were treated with curcumin at different weight ratios.

The presence of magnetic core in the composition is beneficial for using it as a contrast enhancement agent in magnetic resonance imaging (MRI). The synthesized nanoparticles can be a used as a multifunctional probe that can be used in targeted drug delivery, magnetic hyperthermia and contrast enhancement agent in MRI.

The present invention discloses the process for the synthesis of the composition comprising CD-citrate coated nanoparticles encapsulated with curcumin.

The coated, curcumin loaded, nanoparticles are water dispersible for delivery of curcumin at the cancerous sites. The as-synthesized nanoparticle which forms a stable fluid in water can be effectively used for targeting and delivery of hydrophobic drug to the affected site.

In an aspect, the individual components of the composition comprising super paramagnetic iron oxide nanoparticles, β-cyclodextrin, citric acid and curcumin are known to be biocompatible and non-toxic for biomedical applications. The composition is applicable to other hydrophobic entities and anti cancer drugs selected from, but not limited to cisplatin, doxorubicin, taxol, methotrexate, vincritine and such like.

EXAMPLES

Following examples are given by way of illustration and therefore should not be construed to limit the scope of the invention Example 1

Materials: Ferric chloride hexahydrate (≥98%), ferrous chloride tetrahydrate (99%), citric acid monohydrate, curcumin and β-cyclodextrin were purchased from Sigma Aldrich. Ammonium hydroxide (25%), dimethyl sulphoxide (DMSO), nitric acid and 2-propanol were procured from Merck. All the chemicals were used without further purification and double distilled water was used throughout this work.

Preparation of CD-CIT complex: 3 g of β-cyclodextrin and 1 g of citric acid was dissolved in 10 ml of water and the mixture was stirred at 80° C. for three hours. The transparent solution obtained was treated with 2-propanol, which gave a white precipitate. The product was washed thoroughly to remove unreacted components and further dried at 60° C. for 24 hours to get the white CD-CIT complex. The formation of the product was confirmed by FT-IR.

Example 2

Preparation of Surface Functionalized Magnetite Nanoparticles:
Magnetite nanoparticles were prepared by the reverse co-precipitation method. A mixed solution of 2 mmol of $FeCl_3.6H_2O$ and 1 mmol of $FeCl_2.4H_2O$ in water was added to 100 ml of 19% ammonium hydroxide solution under argon atmosphere. The mixture was stirred well for complete formation and growth of magnetite nanoparticles. The nanoparticles were washed with distilled water to remove excess base. Then the pH was brought down to 7 by washing with water and the resultant nanoparticles were re-dispersed in 100 ml distilled water. 2 g of the CD-CIT complex dissolved in water was added drop-wise to the dispersion and stirred for 4 hours at 80° C. The stable dispersion obtained was then dialyzed against water for three days to remove excess CD-CIT complex. The dispersion was then dried at 70° C. to get solid nanoparticles. The coated nanoparticles were well dispersible in water and at the physiological pH to form a nanofluid. The sample was labeled as CDmf. Citric acid coated magnetite nanoparticles were also synthesized following the same procedure for comparison. The nanoparticles coated with citric acid also formed stable dispersion in aqueous media and was labeled as CITmf. Uncoated nanoparticles were also prepared under the same reaction conditions and labeled as Unmf.

Magnetite nanoparticles directly coated with curcumin was synthesized by the procedure reported earlier. A mixture of ferric chloride hexahydrate and ferrous chloride tetrahydrate, taken in the molar ratio of 2:1, was added to ammonia solution to form magnetite nanoparticles. After stirring for 30 minutes, dilute nitric acid was added to bring down the pH to ~8-9. Curcumin solution at the same pH was added and the dispersion was stirred for the effective coating of curcumin to magnetite nanoparticles. The final dispersion was dialyzed against water to remove unreacted excess curcumin and ammonia. The dispersion was dried to get a powder which forms stable dispersion in dimethyl sulfoxide. The curcumin encapsulated sample was labeled as CURmf.

Example 3

Preparation of CUR Inclusion Complex:

20 mg of the CD-CIT coated sample (CDmf) was dispersed in 30 ml water in a 50 ml vial. To this dispersion, varying amounts of curcumin (10 mg, 20 mg and 30 mg), dissolved in 1 ml acetone, were added while stirring gently. The mixture was stirred for 6 hours to evaporate acetone. The dispersion was then stirred overnight and centrifuged at 5000 rpm for 5 minutes. The supernatant liquid which contains highly water dispersed inclusion complex was dried and stored at 5° C. for further use. The resultant inclusion complexes were labeled as CDmf10, CDmf20 and CDmf30. Inclusion complexes were also prepared using CD alone and the CD-CIT conjugate using 20 mg curcumin and 20 mg of the compound. They were designated as CD20 and CD-CIT20, respectively.

Example 4

Curcumin Loading Studies:

1 mg of the solid curcumin inclusion complex was dispersed in 10 ml dimethyl sulfoxide (DMSO) to extract the curcumin to the solvent. This dispersion was shaken on a vortex shaker for 24 hours at room temperature. The vial containing the dispersion was covered with an aluminium foil to prevent exposure to light. The dispersion was then centrifuged at 10000 rpm to remove the curcumin-free CD-CIT coated sample and the clear yellow supernatant solution of curcumin in DMSO was collected and used for estimation. The amount of curcumin released was estimated from the absorbance measured at 425 nm using a standard graph of absorbance of curcumin dissolved in DMSO.

The curcumin entrapment efficiency (EE) is calculated using the formula:

$$EE(\%) = \frac{\text{mass of curcumin trapped}}{\text{mass of curcumin used}} \times 100$$

In Vitro Release:

The release of curcumin from the CD-CIT coated sample was done at pH 7.4 and pH 5.5, by the dialysis bag method. The CDmf20 sample which showed maximum curcumin loading was dispersed in the phosphate buffer (pH=7.4) at a concentration of 1 mg/ml, sonicated to form a stable dispersion and was transferred to a dialysis bag. The dialysis bag tied at both ends was immersed in 50 ml buffer solution and stirred gently. 2 ml of the buffer was withdrawn at particular intervals and replenished with the same amount of fresh buffer. The absorbance was measured at 425 nm, the $\lambda_{max}$ for curcumin. The amount of curcumin released was then plotted against time. Release rate of curcumin was also determined using acetate buffer (pH=5.5) using the same procedure.

Figure 3:
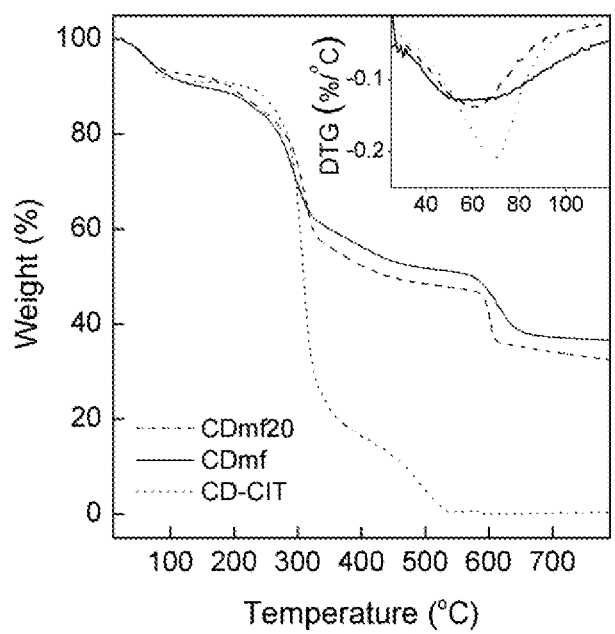
FIG. 3 depicts TGA curves of the CD-CIT complex, CDmf and curcumin loaded CDmf (CDmf20). The inset shows the corresponding differential thermograms (DTG).

As seen in the FIG. 3, the amount of CUR released from β-CD cavity is less at pH 5.5 initially compared to pH 7.4. In the case of CDmf there is an initial burst release whereas the curcumin directly coated to magnetite nanoparticles shows a pulsatile release at the initial stage itself.

Characterization:

Phase purity of the iron oxide nanoparticles was determined by powder X-ray diffraction (XRD) using a PANalytical X'PERT PRO model X-ray diffractometer, in the 2θ range of 10 to 80 degrees, using Cu Kα radiation. TEM analysis was performed on a FEI, TECNAI G2 TF30 instrument. Samples were prepared by placing a drop of dilute dispersion on a carbon coated 200 mesh copper grid and imaged at an accelerating voltage of 300 kV. Zeta potential and hydrodynamic particle size were measured using the dynamic light scattering (DLS) technique using a Brookhaven instruments 90Plus Particle Size Analyzer equipped with a 632.8 nm laser. Infrared spectra were recorded on a Tensor 27 Bruker FT-IR spectrometer, using KBr pellets, in the frequency range of 4000-400 cm$^{-1}$. Thermogravimetric analysis (TGA) of the synthesized samples, in air, was performed on a Perkin-Elmer TGA7 analyzer.

Magnetic measurements were carried out on a Quantum Design MPMS 7TSQUID-VSM. Zero field cooled (ZFC) and field cooled (FC) magnetization measurements were carried out in an applied field of 5 mT (50 Oe) and magnetization versus field measurements, at room temperature, were carried out from −3 T to +3 T. UV-Visible spectra were recorded using a Cary 5000 UV-Vis-NIR spectrophotometer and the measurements were carried out in a Quartz cell of 10 mm path length. The absorbance measurements for the study of curcumin release were also done on the same instrument. Fluorescence measurements were performed using a Photon Technology International fluorescence QM40 spectrophotometer with a Quartz cell of 10 mm path length. The $T_1$ and $T_2$ relaxation studies were done on a Bruker AV400 NMR spectrometer at a magnetic field of 9.4 Tesla and 400 MHz frequency.

The IR spectra of CD, citric acid, CD-CIT complex and CDmf20 are shown in FIG. 1. The spectra of the CD-CIT complex resemble the spectra of CD. The major bands at 3350 cm$^{-1}$, 2925 cm$^{-1}$, 1158 cm$^{-1}$ and 1029 cm$^{-1}$ of CD correspond to the stretching vibrations of —OH, —CH$_2$, —C—C and bending vibration of —OH groups, respectively. The band at 1645 cm$^{-1}$ corresponds to the H—O—H deformation band of water present in the cavity of CD. The band at 1750 cm$^{-1}$ in the spectra of citric acid is due to the vibration of the C=O group of the carboxylic acid and this band is shifted to 1730 cm$^{-1}$ in CD-CIT due to the formation of ester. The band at 1730 cm$^{-1}$, which is due to the C=O stretching of the ester group, is a clear indication for the formation of the CD-CIT conjugate. The intensity of this band of CD-CIT is reduced in CDmf, after coating on the magnetite nanoparticles, indicating that the CD-CIT conjugate binds to the nanoparticle via the C=O group of the citric acid. The bands in the IR spectra of the coated nanoparticles resemble that of the CD-CIT conjugate indicating the bonding of the conjugate to nanoparticles surface. The band at 1645 cm$^{-1}$ corresponding to the vibrations of water in the CD cavity is found to be retained in the coated nanoparticles also, indicating that the iron oxide nanoparticles are not occupied inside the cavity and binds to the CD-CIT complex without disturbing the cavity.

Figure 2:
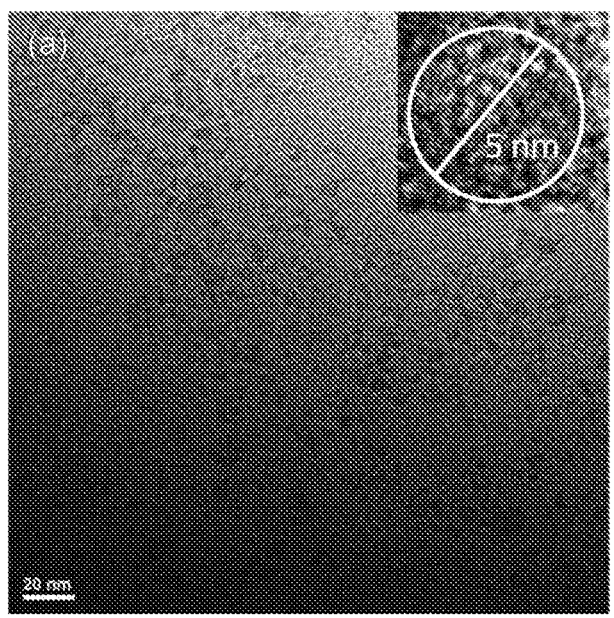
FIG. 2 depict (a) TEM image of CDmf with the inset showing a single particle of size 5 nm, and (b) the log-normal size distribution from DLS measurement showing a mean particle size of 7.7 nm.
Figure 2:
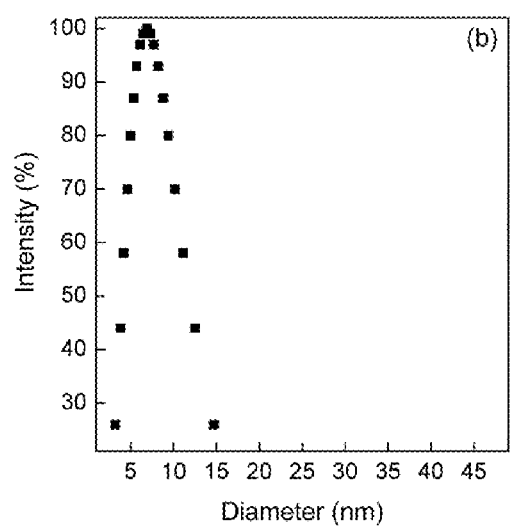

The average crystallite size of the CDmf nanoparticles is calculated as 5 nm from the XRD pattern using the Scherrer equation. The TEM image in FIG. 2(a) shows isolated particles with average particle size of 5 nm, comparable to the crystallite size. Average particle size of 7.7 nm, with a polydispersity of 0.261, is obtained from DLS measurements as shown in FIG. 2(b).

TGA curve of CDmf is compared with that of CD and the CD-CIT conjugate in FIG. 3. The total weight loss for CDmf is about 60% and the weight loss path resembles that of bare CD-CIT conjugate, except for a shift in the third weight loss to higher temperatures. Dehydration of CDmf and CD-CIT caused a total mass loss of 8.2% and 8.5% (first weight loss below 100° C.), and this corresponds to loss of 6.3 and 6.1 water molecules, respectively, from the cavity of CD. The dehydration of CDmf20 results in a mass loss of 6.1%, indicating the removal of 4.5 water molecules from the CD cavity.

Figure 4:
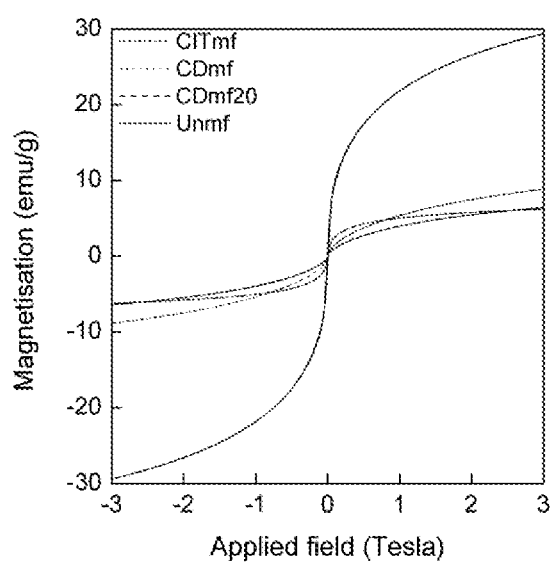
FIG. 4 depict Magnetization curves of the uncoated and different coated iron oxide nanoparticles, measured at room temperature.

The M vs H curves of the iron oxide samples measured at room temperature, before and after surface modifications, are shown in FIG. 4.

Figure 5C:
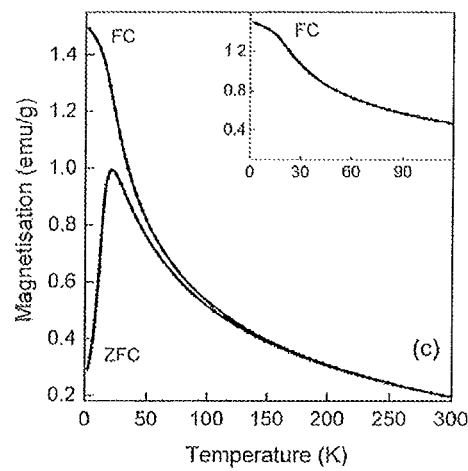
FIG. 5 depict ZFC and FC magnetization curves of (a) uncoated magnetite nanoparticles (Unmf), (b) CIT coated nanoparticles (CITmf), (c) CD-CIT coated nanoparticles (CDmf), and (d) CUR loaded CDmf nanoparticles (CDmf20), measured in a field of 50 Oe. The insets of (c) and (d) show the enlarged FC curves at low temperatures.
Figure 5D:
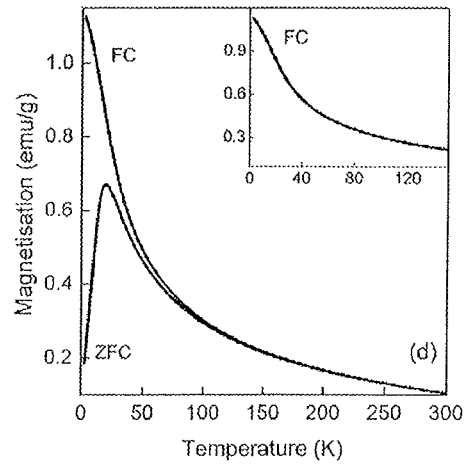

The zero field cooled (ZFC) and field cooled (FC) magnetization curves of the uncoated and the different coated nanoparticles are compared in FIG. 5. The superparamagnetic blocking temperature ($T_B$), corresponding to the temperature at which a maximum is observed in the zero field cooled (ZFC) magnetization curve, for the uncoated (Unmf) and citric acid coated (CITmf) samples are obtained as 110 K and 40 K, respectively.

CDmf and the inclusion complex CDmf20 show almost comparable values of $T_B$ as 20 K. The FC curve of Cdmf shows a saturating trend at very low temperatures (inset of FIG. 5(c)) whereas this trend is not observed for CDmf20 (inset of FIG. 5(d)).

Figure 6:
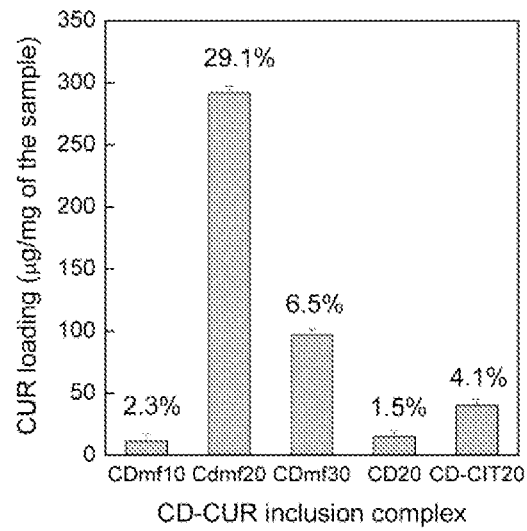
FIG. 6 depict graph showing the amount of CUR loaded per mg of the sample (CDmf10, CDmf20 and CDmf30) compared with CUR inclusion complex of bare β-CD (CD20) and CD-CIT (CD-CIT20). The numbers in percentage represent the loading efficiency.

The curcumin inclusion complexes, CDmf10, CDmf20 and CDmf30, are analyzed for their curcumin loading capacity (FIG. 6). The encapsulation efficiency was found to be higher in the case of 1:1 weight ratio of the sample and curcumin (CDmf20) is used (20 g each). The encapsulation efficiency of the coated nanoparticles is also compared with that of bare CD as well as the CD-CIT complex (FIG. 6). Higher efficiency is observed for CD-CIT (4.1%) compared to CD (1.5%). The solubility of bare β-cyclodextrin in water is found to be ~18 mg/ml, whereas the solubility of CD-CIT complex is obtained as ~60 mg/ml. PLGA nanoparticles show a maximum curcumin loading of about 5-10%.

The zeta potential of the different formulations is measured by dispersing them in water. The zeta potential of CDmf is measured as −19.2 mV. CITmf also gave stable water dispersion with a zeta potential of −21.8 mV. The zeta potential for CDmf10, CDmf20 and CDmf30 are obtained as −33.2, −30.3 and −35.8 mV, respectively, indicating the high stability of the dispersions.

Figure 7:
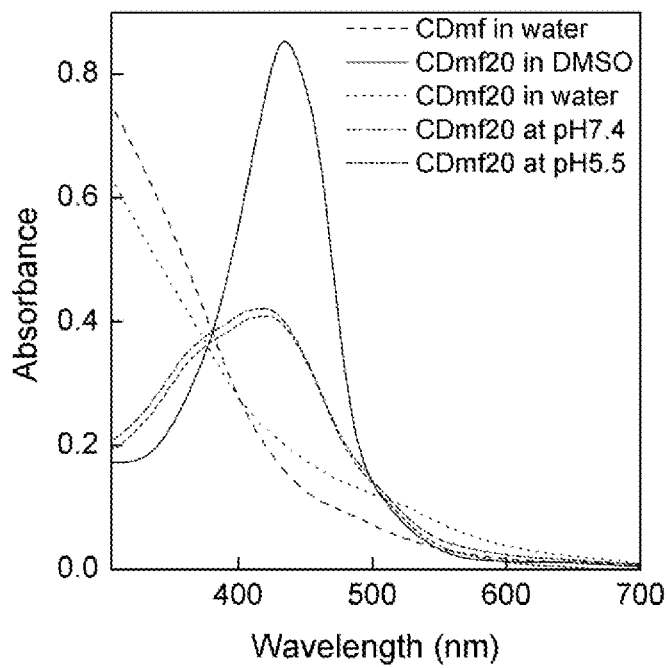
FIG. 7 depicts UV-visible spectra of CD-CIT coated (CDmf) and curcumin loaded (CDmf20) nanoparticles dispersed in water. Spectra of CDmf20 dispersed in DMSO as well as in buffer solutions (pH of 7.4 and 5.5) are also shown which show the distinct peak of curcumin.

The UV-visible spectra also do not show any sharp peak at 425 nm which is the characteristic absorption maximum of curcumin. However, the inclusion complex once treated with dimethyl sulfoxide (DMSO) gives the characteristic peak of curcumin, as shown in FIG. 7, where the UV spectra of CDmf dispersed in different media are compared.

Figure 8:
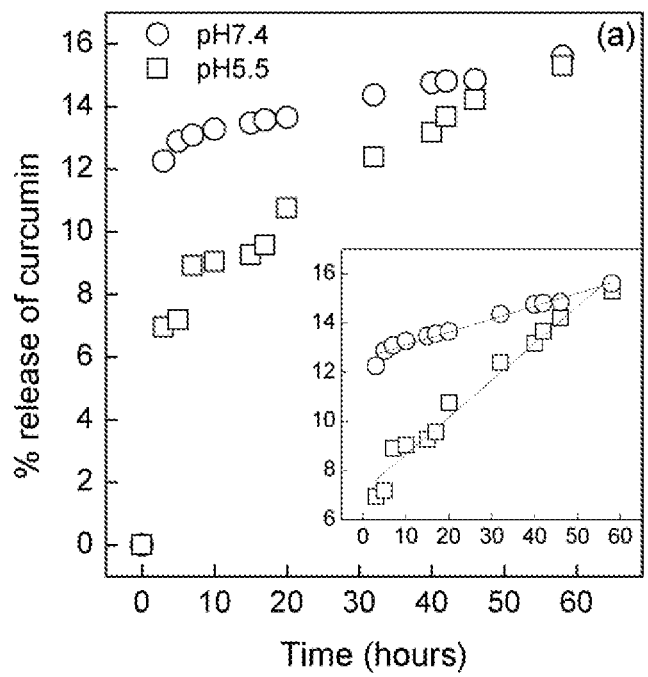
FIG. 8 depicts the drug (curcumin) release profile of (a) CDmf and (b) CURmf at pH7.4 and 5.5. The inset of (a) shows the zero order fitting curves of the release profile.
Figure 8:
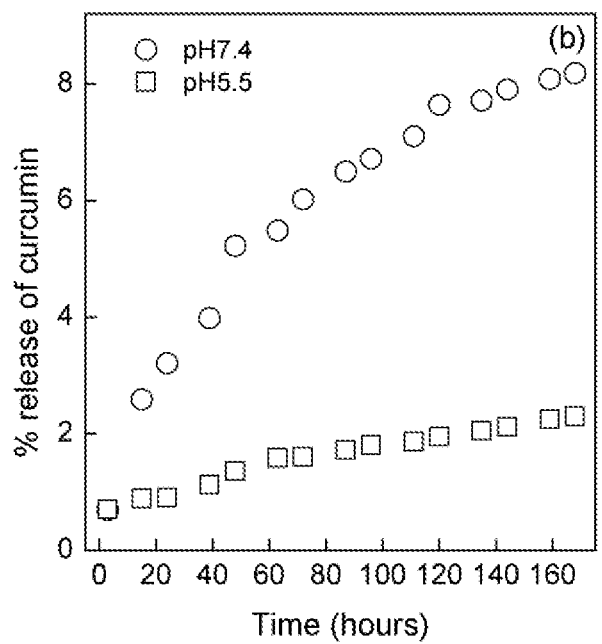

The release profile of CUR from CDmf20 sample was analyzed at the physiological pH 7.4 and that of the diseased cells pH 5.5. As shown in FIG. 8, the amount of CUR released from the CD cavity is very low at pH 5.5, initially, compared to that released at the physiological pH 7.4.

The release profile of CURmf follows the zero order kinetics at both the investigated pH values from the initial time itself whereas the CDmf shows a burst release of CUR followed by constant release. The amount of CUR released from the CDmf sample at a particular time is larger than that compared to CURmf.

Figure 9:
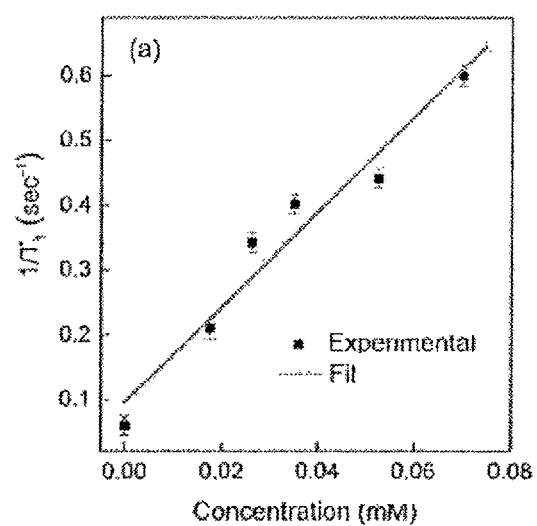
FIG. 9 depicts the reciprocals of (a) spin lattice ($T_1$) and (b) spin-spin ($T_2$) relaxation times plotted against concentration.
Figure 9:
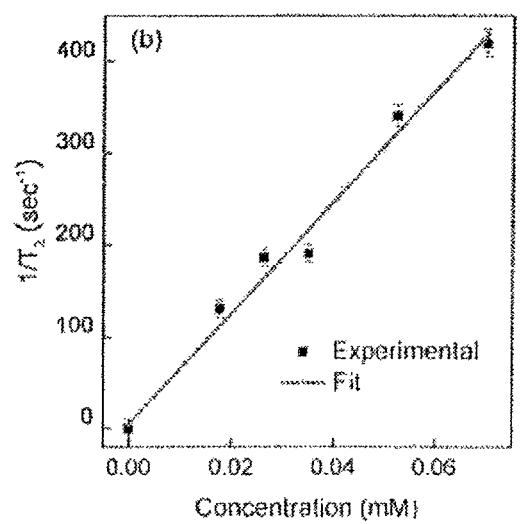

The relaxivity of cyclodextrin coated magnetite nanoparticles is measured on an NMR spectrophotometer at a magnetic field of 9.4 T and frequency of 400 MHz. The CDmf sample was dispersed in water at different concentrations and the spin-lattice relaxation time $T_1$ and spin-spin relaxation time $T_2$ are measured. The reciprocals of the relaxation times are plotted against concentration (FIG. 9) to obtain the corresponding relaxivity values $r_1$ and $r_2$ which describe the ability to shorten the relaxation times per millimole of the concentration of contrast agent. The relaxivity values, $r_1$ and $r_2$, calculated from the slopes of the plots are 0.0082 mM$^{-1}$s$^{-1}$ and 6.875 mM$^{-1}$s$^{-1}$, respectively. The $r_2/r_1$ ratio is obtained as 838. The $r_2$ and $r_1$ values are calculated by considering the particle diameter as 5 nm as obtained from TEM, which will have approximately 880 magnetic iron ions. The $r_2/r_1$ ratio is larger than the minimum threshold (=2) value required to be used as an effective contrast agent.

Advantages of the Invention

Higher loading of drug
Smaller hydrodynamic diameter of complex facilitating better lodging of hydrophobic drug

The invention claimed is:

1. Beta-cyclodextrin-citrate coated magnetic nanoparticles having a size of 3 to 10 nm, wherein the beta-cyclodextrin-citrate coated magnetic nanoparticles are free of Beta-cyclodextrin-citrate gum Arabic modified nanoparticles, and
wherein the beta-cyclodextrin-citrate coated magnetic nanoparticles are loaded with a hydrophobic drug.

2. In a targeted drug delivery method the improvement comprising using the Beta-cyclodextrin-citrate coated magnetic nanoparticles as claimed in claim 1 to deliver the drug.

3. The Beta-cyclodextrin-citrate coated magnetic nanoparticles as claimed in claim 1, wherein the hydrophobic drug is one or more drug selected from the group consisting of curcumin, doxorubicin, taxol, methotrexate, and vincristine.

4. The Beta-cyclodextrin-citrate coated magnetic nanoparticles as claimed in claim 1, wherein the hydrophobic drug is curcumin.

5. In an MRI Scanning method the improvement comprising using the Beta-cyclodextrin-citrate coated magnetic nanoparticles as claimed in claim 1 as contrast enhancement agents.

* * * * *